US010413209B2

(12) United States Patent
Huang

(10) Patent No.: US 10,413,209 B2
(45) Date of Patent: Sep. 17, 2019

(54) METHOD AND APPARATUS FOR IDENTIFYING THE URETER DURING A MINIMALLY-INVASIVE PROCEDURE

(71) Applicant: The Methodist Hospital, Houston, TX (US)

(72) Inventor: Albert Yung-Hsiang Huang, Houston, TX (US)

(73) Assignee: The Methodist Hospital, Houston, TX (US)

( * ) Notice: Subject to any disclaimer, the term of this patent is extended or adjusted under 35 U.S.C. 154(b) by 379 days.

(21) Appl. No.: 15/118,689

(22) PCT Filed: Feb. 12, 2015

(86) PCT No.: PCT/US2015/015671
§ 371 (c)(1),
(2) Date: Aug. 12, 2016

(87) PCT Pub. No.: WO2015/123441
PCT Pub. Date: Aug. 20, 2015

(65) Prior Publication Data
US 2017/0042445 A1 Feb. 16, 2017

Related U.S. Application Data

(60) Provisional application No. 61/938,767, filed on Feb. 12, 2014.

(51) Int. Cl.
*A61B 5/00* (2006.01)
*A61B 5/0488* (2006.01)
(Continued)

(52) U.S. Cl.
CPC .......... *A61B 5/04882* (2013.01); *A61B 1/307* (2013.01); *A61B 5/0492* (2013.01);
(Continued)

(58) Field of Classification Search
CPC .............. A61B 5/0488; A61B 5/04882; A61B 5/04884; A61B 5/0492; A61B 5/1107; A61B 1/307
See application file for complete search history.

(56) References Cited

U.S. PATENT DOCUMENTS 5,470,308 A * 11/1995 Edwards ............ A61B 10/0233
604/22
5,531,741 A 7/1996 Barbacci
(Continued)

FOREIGN PATENT DOCUMENTS

| EP | 2684525 | 1/2014 |
| WO | WO 2001/007111 | 2/2001 |

(Continued)

OTHER PUBLICATIONS

Chahin et al., "The Implications of Lighted Ureteral Stenting in Laparoscopic Colectomy", JSLS, vol. 6, 2002, pp. 49-52.
(Continued)

*Primary Examiner* — Max F Hindenburg
(74) *Attorney, Agent, or Firm* — Wilson Sonsini Goodrich & Rosati

(57) ABSTRACT

A method for identifying a ureter during a medical procedure, the method comprising: providing an electrical stimulator comprising: a shaft having at least one electrode; and a power supply connected to the at least one electrode for providing an electrical signal to the at least one electrode; advancing the shaft so that the at least one electrode contacts tissue; operating the power supply so that the electrical signal is applied to the tissue; and visually observing the tissue to determine the presence of a ureter in the tissue.

19 Claims, 11 Drawing Sheets

(51) Int. Cl.
*A61B 1/307* (2006.01)
*A61B 5/0492* (2006.01)
*A61B 5/11* (2006.01)
*A61B 5/20* (2006.01)
*A61B 17/34* (2006.01)
*A61N 1/05* (2006.01)
*A61N 1/36* (2006.01)
*A61N 1/378* (2006.01)
*A61B 90/00* (2016.01)

(52) U.S. Cl.
CPC ............ *A61B 5/1107* (2013.01); *A61B 5/20* (2013.01); *A61B 5/425* (2013.01); *A61B 5/4283* (2013.01); *A61B 5/4887* (2013.01); *A61B 5/7415* (2013.01); *A61B 17/3423* (2013.01); *A61N 1/0521* (2013.01); *A61N 1/36007* (2013.01); *A61N 1/378* (2013.01); *A61B 2090/065* (2016.02)

(56) References Cited

U.S. PATENT DOCUMENTS

| | | | | |
|---|---|---|---|---|
| 7,278,994 | B2* | 10/2007 | Goble | A61B 17/3423 606/41 |
| 7,331,957 | B2* | 2/2008 | Woloszko | A61B 18/1402 604/114 |
| 7,645,286 | B2* | 1/2010 | Catanese | A61B 17/0401 606/151 |
| 8,845,545 | B2* | 9/2014 | Folkerts | A61B 5/04882 600/557 |
| 8,989,861 | B2* | 3/2015 | Su | A61B 5/04882 607/41 |
| 2009/0030473 | A1 | 1/2009 | Khawaled et al. | |
| 2009/0125025 | A1 | 5/2009 | Rosemberg | |
| 2013/0165944 | A1 | 6/2013 | Gal et al. | |
| 2013/0267874 | A1 | 10/2013 | Marcotte et al. | |
| 2014/0018668 | A1 | 1/2014 | Zheng et al. | |

FOREIGN PATENT DOCUMENTS

| | | |
|---|---|---|
| WO | WO 2007/127209 | 11/2007 |
| WO | WO 2010/067360 | 6/2010 |
| WO | WO 2013/090827 | 6/2013 |

OTHER PUBLICATIONS

Da Silva et al., "Role of prophylactic ureteric stents in colorectal surgery," Asian Journal of Endoscopic Surgery, vol. 5, 2012, pp. 105-110.

Fanning et al., "Cost Analysis of Prophylactic Intraoperative Cystoscopic Ureteral Stents in Gynecologic Surgery", J Am Ost Assoc., vol. 111, No. 12, 2011, pp. 667-669.

Roshani et al., "Pharmacological Modulation of Ureteral Peristalsis in a Chronically Instrumented Conscious Pig Model. I: Effect of Cholinergic Stimulation and Inhibition", Journal of Urology, vol. 170, No. 1, 2003, pp. 264-267.

Schimpf et al., "Universal ureteral stent placement at hysterectomy to identify ureteral injury: a decision analysis", BJOG, vol. 115, 2008, pp. 1151-1158.

* cited by examiner

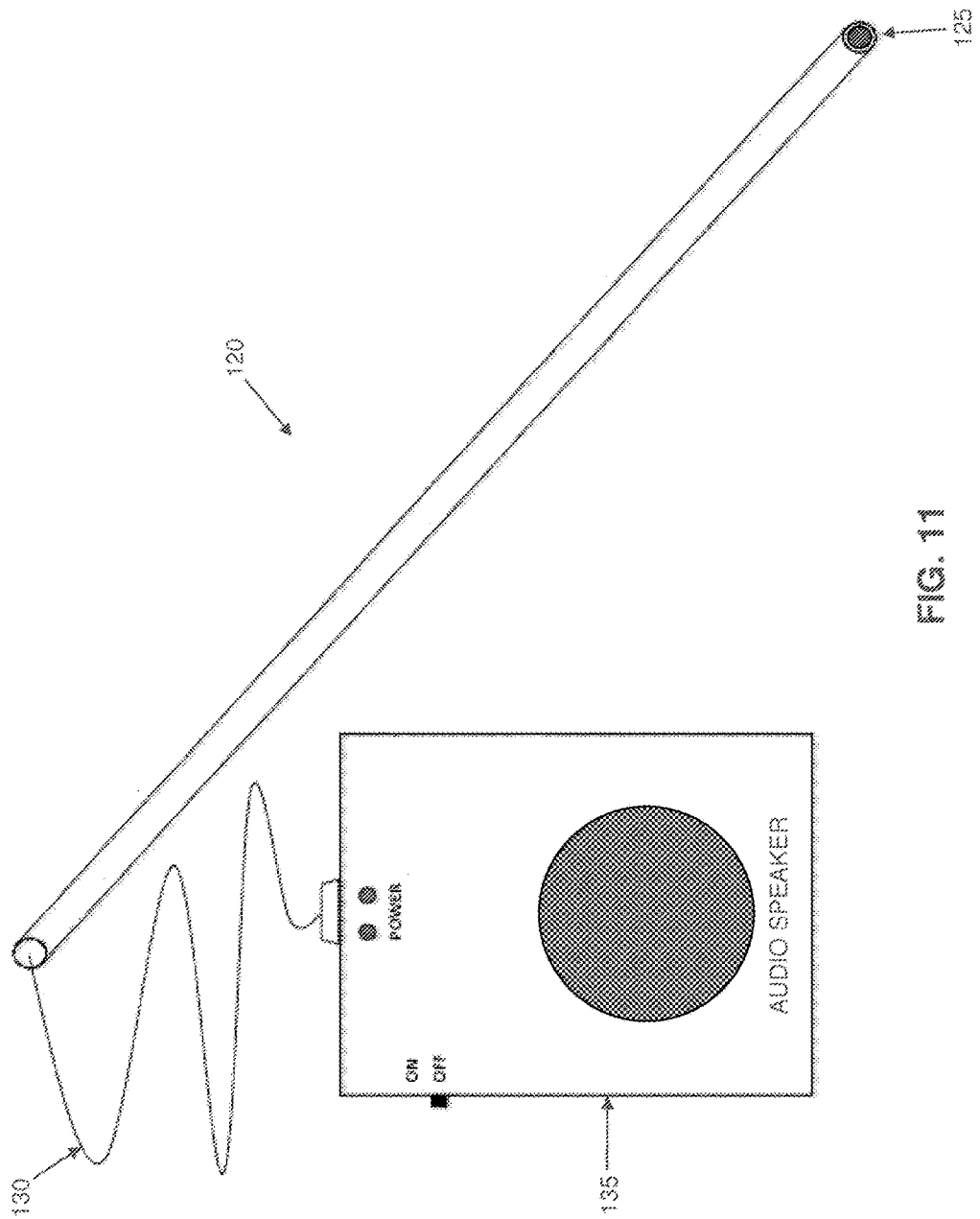

METHOD AND APPARATUS FOR IDENTIFYING THE URETER DURING A MINIMALLY-INVASIVE PROCEDURE

REFERENCE TO PENDING PRIOR PATENT APPLICATION

This patent application claims benefit of prior U.S. Provisional Patent Application Ser. No. 61/938,767, filed Feb. 12, 2014 by The Methodist Hospital and Albert Yung-Hsiang Huang for MINIMALLY INVASIVE URETER IDENTIFICATION DEVICE, which patent application is hereby incorporated herein by reference.

FIELD OF THE INVENTION

This invention relates to medical procedures and apparatus in general, and more particularly to methods and apparatus for identifying the ureter.

BACKGROUND OF THE INVENTION

In minimally-invasive surgery, the identification of anatomical structures must be done through knowledge of the anatomy and knowledge of anatomical landmarks, given the lack of true tactile feedback for the surgeon. When operating in the lower abdomen and pelvis, surgeons of many specialties (e.g., general surgery, colorectal surgery, transplant surgery, urology, obstetrics, gynecology, etc.) are acutely aware of the need for accurate identification of the ureter in order to prevent potentially catastrophic injury to the ureter. Although identification of the ureter may appear to be a simple and routine visual task, difficulties lie in "hostile" abdomens where there have been prior surgeries, inflammation and/or scarring, or if tissue planes are not well defined.

It has been reported that the incidence of ureteral injuries in gynecological procedures is upwards of 3.2%, with 70% of the ureteral injuries not being discovered until after completion of the procedure.

A ureteral injury can result in significant morbidity to the patient. In addition, a ureteral injury can also lead to longer operating room (OR) times (due to the need for ureteral repairs), the involvement of specialists, the potential need for long term ureteral stent placements, and long term effects (such as scarring) that may lead to kidney damage. All of these are costly, both to the patient as well as the hospital, inasmuch as medical insurance generally does not cover costs related to complications from an operation.

Several different approaches are currently used to identify the ureter during a minimally-invasive procedure.

Where the ureter is easily identified visually, the surgeon generally confirms ureter identification by lightly compressing the ureter with an instrument (e.g., graspers, forceps, etc.) and observing the resulting visible contractions of the ureter up and down its length as a response to the instrument stimulus. However, as noted above, the ureter is frequently difficult to identify visually and, even where it is relatively easily identifiable, the ureter does not always generate visually-detectable contractions as a result of an instrument stimulus. Furthermore, care must be taken with this approach to avoid injuring to the ureter.

For these reasons, surgeons have turned to the pre-operative (but post-anesthesia) placement of ureteral stents via cystoscopy. Where the surgery is an "open" procedure, the surgeon can detect the ureteral stent by manual sensation. Where the surgery is a "closed" procedure (e.g., a minimally-invasive procedure), light-emitting stents may be utilized, with the light-emitting stents being detected visually during the minimally-invasive procedure.

However, with ureteral stents, a urologist must generally be available to deploy the ureteral stents up each ureter from the bladder. This process may be time-consuming, which leads to a longer OR time (and thus longer anesthesia time) and comes with its own risks of ureter injury and infection, due to the need to place a foreign object in the ureter. Furthermore, the average cost of the ureteral stent placement procedure is approximately $1500, with studies demonstrating a significant decrease (e.g., up to 85%) in procedural profit margin where prophylactic ureteral stenting is utilized. In addition, even where a ureteral stent is used, ureter injury can still occur. Many experienced surgeons have noted that, at times, the ureteral stent only serves to notify them that they have injured the ureter, i.e., when the surgeons see the ureteral stent exposed inside the abdomen.

Even with these drawbacks, pre-operative ureteral stent placement is quickly becoming routine in hospitals nationwide due to the need to reliably identify the ureter during surgery.

Thus there is a need for a new method and apparatus for reliably identifying the ureter in both open and closed procedures and which eliminates the need for pre-operative ureteral stent placement, whereby to avoid the risks and costs associated with pre-operative ureteral stent placement.

SUMMARY OF THE INVENTION

The present invention provides a new method and apparatus for reliably identifying the ureter in both open and closed procedures and which eliminates the need for pre-operative ureteral stent placement, whereby to avoid the risks and costs associated with pre-operative ureteral stent placement.

In accordance with the present invention, there is provided a novel electrical stimulator which generates a low-level electrical current (preferably but not necessarily in a pulsatile form), such that when the tip of the electrical stimulator is positioned near the ureter, the low-level electrical current provided by the electrical stimulator will cause the ureteral muscles to contract up and down the length of the ureter. This results in movement of the anatomy that can be visualized by the surgeon, even if the ureter is obscured by other tissues (e.g., scar tissue). In this way, the location of the ureter can be identified (or confirmed) so that the ureter may be avoided during the surgical procedure.

In one preferred form of the present invention, there is provided a method for identifying a ureter during a medical procedure, said method comprising:
providing an electrical stimulator comprising:
a shaft having at least one electrode; and
a power supply connected to said at least one electrode for providing an electrical signal to said at least one electrode;
advancing said shaft so that said at least one electrode contacts tissue;
operating said power supply so that said electrical signal is applied to the tissue; and
visually observing the tissue to determine the presence of a ureter in the tissue.

In another preferred form of the present invention, there is provided an electrical stimulator for identifying a ureter during a medical procedure, said electrical stimulator comprising:
a shaft having a distal end, a proximal end and at least one electrode disposed at said distal end, said shaft having a diameter sized for insertion through an intervening device during a minimally-invasive procedure, and said shaft having a length so that said at least one electrode can contact tissue located at a remote internal site while said proximal end of said shaft remains outside the body of a patient; and a power supply connected to said at least one electrode for providing an electrical signal to said at least one electrode, wherein said electrical signal is configured to elicit a peristaltic response from a ureter when said at least one electrode is positioned so as to deliver said electrical signal to the ureter.

In another preferred form of the present invention, there is provided a method for identifying an anatomical structure during a medical procedure, said method comprising:

providing an electrical stimulator comprising:
a shaft having at least one electrode; and
a power supply connected to said at least one electrode for providing an electrical signal to said at least one electrode;
advancing said shaft so that said at least one electrode contacts tissue;
operating said power supply so that said electrical signal is applied to the tissue; and
visually observing the tissue to determine the presence of the anatomical structure in the tissue.

In another preferred form of the present invention, there is provided an electrical stimulator for identifying an anatomical structure during a medical procedure, said electrical stimulator comprising:

a shaft having a distal end, a proximal end and at least one electrode disposed at said distal end, said shaft having a diameter sized for insertion through an intervening device during a minimally-invasive procedure, and said shaft having a length so that said at least one electrode can contact tissue located at a remote internal site while said proximal end of said shaft remains outside the body of a patient; and a power supply connected to said at least one electrode for providing an electrical signal to said at least one electrode, wherein said electrical signal is configured to elicit a visible response from the anatomical structure when said at least one electrode is positioned so as to deliver said electrical signal to the anatomical structure.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts, and further wherein:

FIG. 11 is a schematic view showing an electromyogram (EMG) probe which may be used in conjunction with the novel electrical stimulator of the present invention.

DETAILED DESCRIPTION OF THE PREFERRED EMBODIMENTS

The present invention provides a new method and apparatus for reliably identifying the ureter in both open and closed procedures and which eliminates the need for pre-operative ureteral stent placement, whereby to avoid the risks and costs associated with pre-operative ureteral stent placement.

In one form of the present invention, there is provided an inexpensive, simple-to-use device that is handheld, disposable and which can be advanced to the surgical site through a cannula during a minimally-invasive procedure so as to electrically stimulate tissue, whereby to identify the ureter from surrounding anatomy. Note that the device can also be advanced to the surgical site through the working channel of an endoscope, or through a working channel of any other device leading to an internal surgical site.

More particularly, when a patient is under general anesthesia and paralyzed for an intraabdominal operation, the "skeletal muscles" of the patient are unable to respond to electrical nerve stimulation. However, "smooth muscles" (which include structures such as the ureter) are able to respond (e.g., contract and peristalse) when electrically stimulated. The present invention utilizes this fact to identify the ureter during a surgical procedure.

In accordance with the present invention, there is provided a novel electrical stimulator which generates a low-level electrical current (preferably but not necessarily in a pulsatile form), such that when the tip of the electrical stimulator is positioned on or near the ureter, the low-level electrical current provided by the electrical stimulator will cause the ureteral muscles to contract up and down the length of the ureter. This results in movement of the anatomy that can then be visualized by the surgeon, even if the ureter is obscured by other tissues (e.g., scar tissue). In this way, the location of the ureter can be identified (or confirmed) so that it may be avoided during the surgical procedure. Note that the electrical stimulator does not need to be positioned directly on the ureter in order to achieve ureter stimulation, it simply needs to be placed close enough to the ureter that the low-level electrical current reaches the ureter.

In one form of the present invention, the electrical stimulator comprises a probe component comprising electrodes and a power supply component housed in a base unit, with the probe component being connected to the power supply component with an external cable (i.e., a "modular construction").

In another form of the present invention, the power supply component is carried by the probe component and the external cabling can be omitted (i.e., an "integrated construction").

Modular Construction

Figure 1:
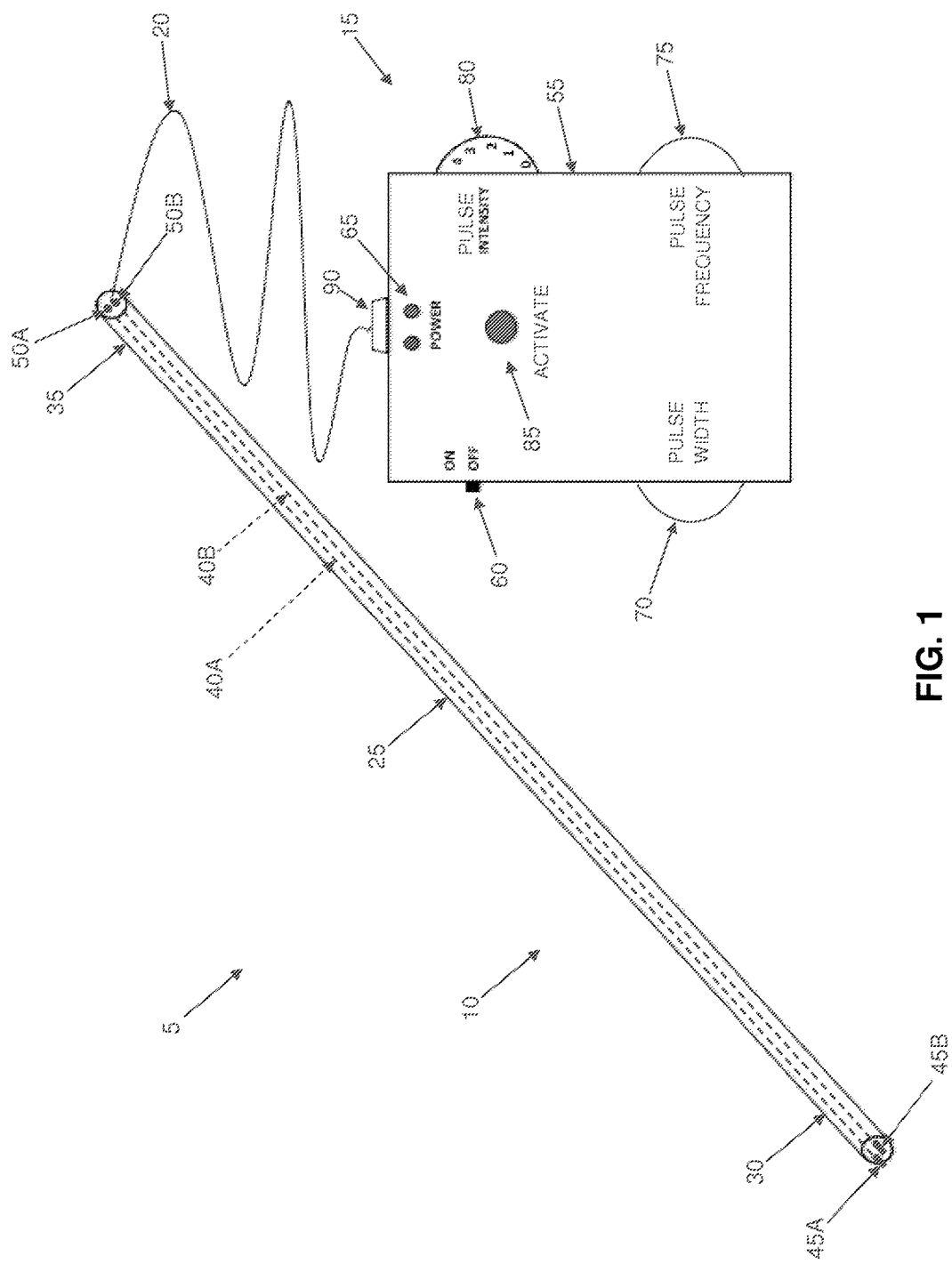
FIG. 1 is a schematic view showing a novel electrical stimulator formed in accordance with the present invention.
Figure 2:
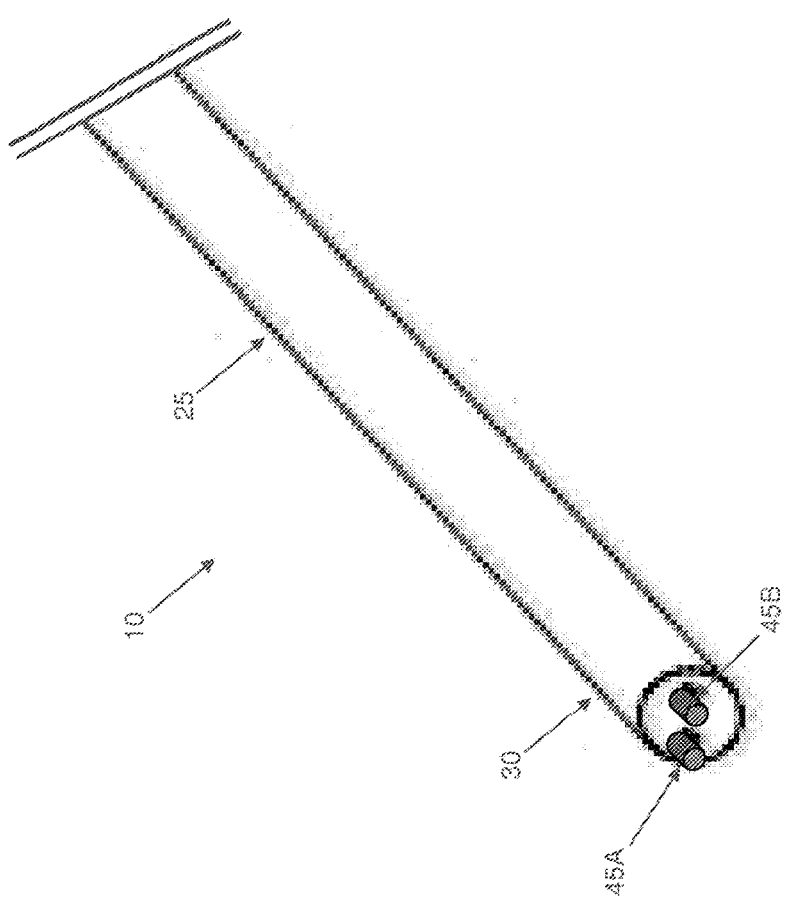
FIG. 2 is a schematic view showing the distal end of the probe of the novel electrical stimulator shown in FIG. 1.

More particularly, in one preferred form of the present invention, and looking now at FIGS. 1 and 2, there is provided a novel electrical stimulator 5 which generally comprises a probe 10 and a power supply 15. A cable 20 connects power supply 15 to probe 10.

Probe 10 generally comprises a shaft 25 having a distal end 30 and a proximal end 35. In one preferred form of the invention, shaft 25 has a length of approximately 330 mm and a diameter of approximately 5 mm. Note that the diameter of probe 10 may be larger or smaller so as to fit through cannulas of different diameters. Note also that the length of shaft 25 may be longer or shorter depending upon the distance to the internal surgical site (e.g., shaft 25 may be longer where novel electrical stimulator 5 is to be used in conjunction with robotic surgical equipment).

A pair of leads 40A, 40B extend through shaft 25 from distal end 30 to proximal end 35. Lead 40A terminates distally in an electrode tip 45A and lead 40B terminates distally in an electrode tip 45B, with electrode tip 45A acting as one of the anode and cathode and electrode tip 45B acting as the other of the anode and cathode. If desired, electrode tip 45A and electrode tip 45B may be separated by an insulating mass which physically separates the anode and cathode from one another so as to ensure that the electrical signal must pass through tissue in contact with the device. If desired, the insulating mass may form part of a blunt tip for shaft 25, with the blunt tip being designed for blunt dissection in the minimally-invasive setting. Lead 40A terminates proximally in an electrical connector 50A and lead 40B terminates proximally in an electrical connector 50B.

Power supply 15 provides the energy source for probe 10. Power supply 15 comprises a base unit 55 housing an internal power supply (not shown) capable of providing a desired electrical signal. In one preferred form of the invention, the electrical signal provided by power supply 15 is a pulsatile signal of variable pulse width (e.g., 25-300 milliseconds), variable pulse frequency (e.g., 1-5 Hz), variable pulse intensity (e.g., 60 mV-500 V) and variable pulse amperage (e.g., 5-200 mA, preferably adjustable in 20 mA increments, although it is preferred that the amperage be limited to 60 mA to minimize patient discomfort and avoid cardiac arrhythmias). To this end, power supply 15 preferably comprises a power on/off switch 60, an associated power on/off indicator 65, a pulse width control 70, a pulse frequency control 75, a pulse intensity control 80 and an activate button 85. Power supply 15 also comprises an electrical connector 90.

Cable 20 connects the output of power supply 15 to electrical connector 50A and electrical connector 50B of probe 10, so that the output of power supply 15 can be applied to electrode tip 45A and electrode tip 45B of probe 10.

Figure 3:
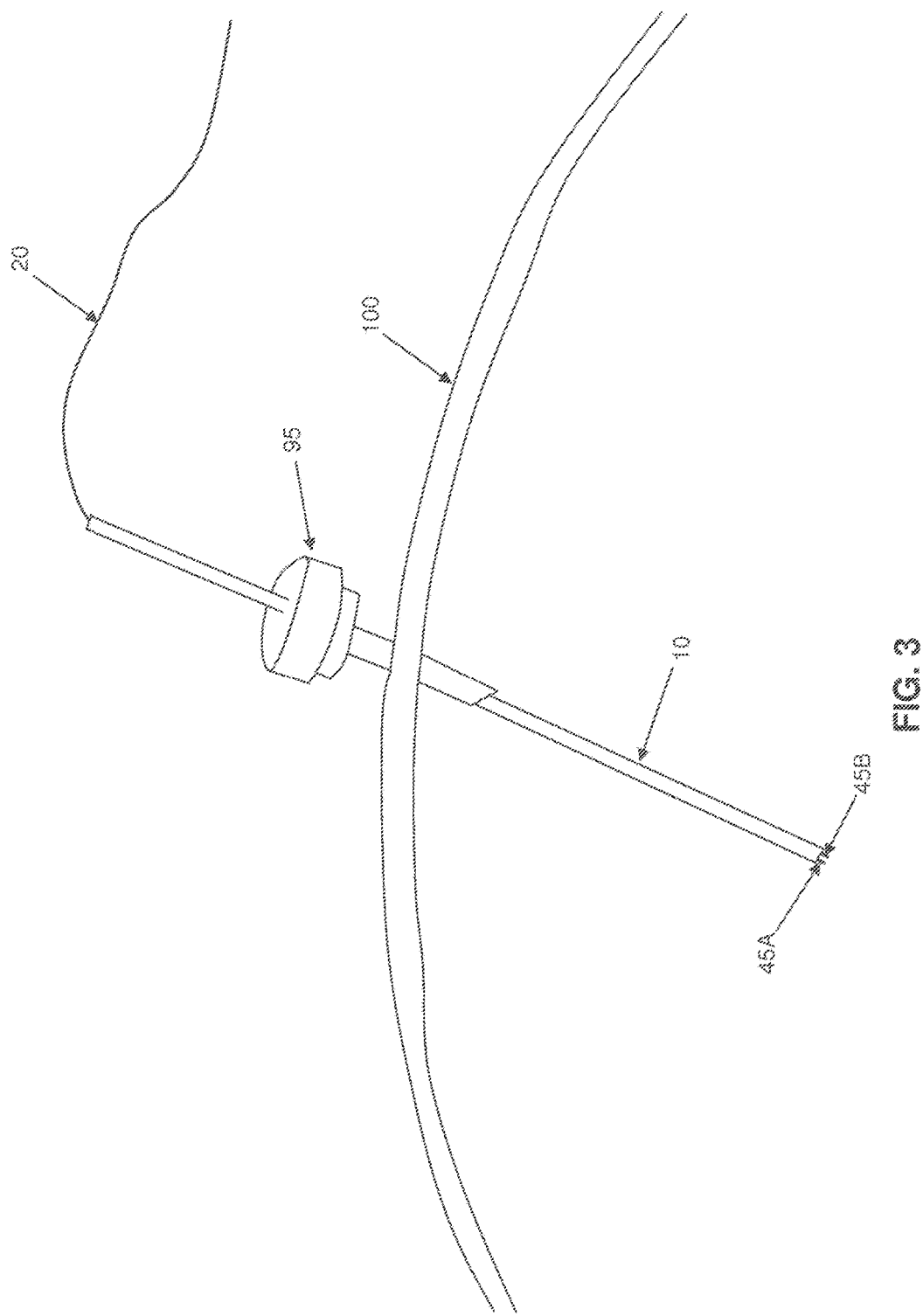
FIG. 3 is a schematic view showing the probe advanced through a cannula so that its distal end is positioned adjacent a surgical site.

In use, cable 20 is connected to probe 10 and power supply 15, power supply 15 is turned on via power on/off switch 60, and pulse width control 70, pulse frequency control 75 and pulse intensity control 80 are all set to appropriate levels. Next, and looking now at FIG. 3, probe 10 is advanced to the surgical site (e.g., through a cannula 95 extending through the skin 100 of a patient). Then probe 10 is advanced to the region where the ureter is believed to lie, electrode tips 45A and 45B are placed against the tissue, and then activate button 85 is depressed so as to apply a low-level pulsatile electrical current to the tissue. When electrode tips 45A and 45B are located in the vicinity of the ureter, the electrical signal will cause the ureter to generate a rhythmic twitch as the ureteral muscles contract up and down the length of the ureter. The surgeon can observe this muscular response of the ureter, whereby to confirm ureter presence as well as the ureter path.

It should be appreciated that the characteristic response of the ureter "smooth muscle" is a propagation of contractile movement that begins at the focus of stimulation. This contraction travels retrograde and antegrade along the length of the ureter. This contraction is easily visualized on the video monitor use in minimally-invasive procedures (e.g., laparoscopic procedures, robotic procedures, etc.) as well as with direct visualization in open surgery settings. The ureter does not need to be fully dissected out from nearby tissue inasmuch as the contraction movements can be seen even with the ureter "smooth muscle" being beneath other tissues such as scar tissue, thin layers of fat or connective tissues.

Figure 4:
FIGS. 4-6 are schematic views showing electrical stimulation of a ureter using the novel electrical stimulator shown in FIG. 1.
Figure 5:
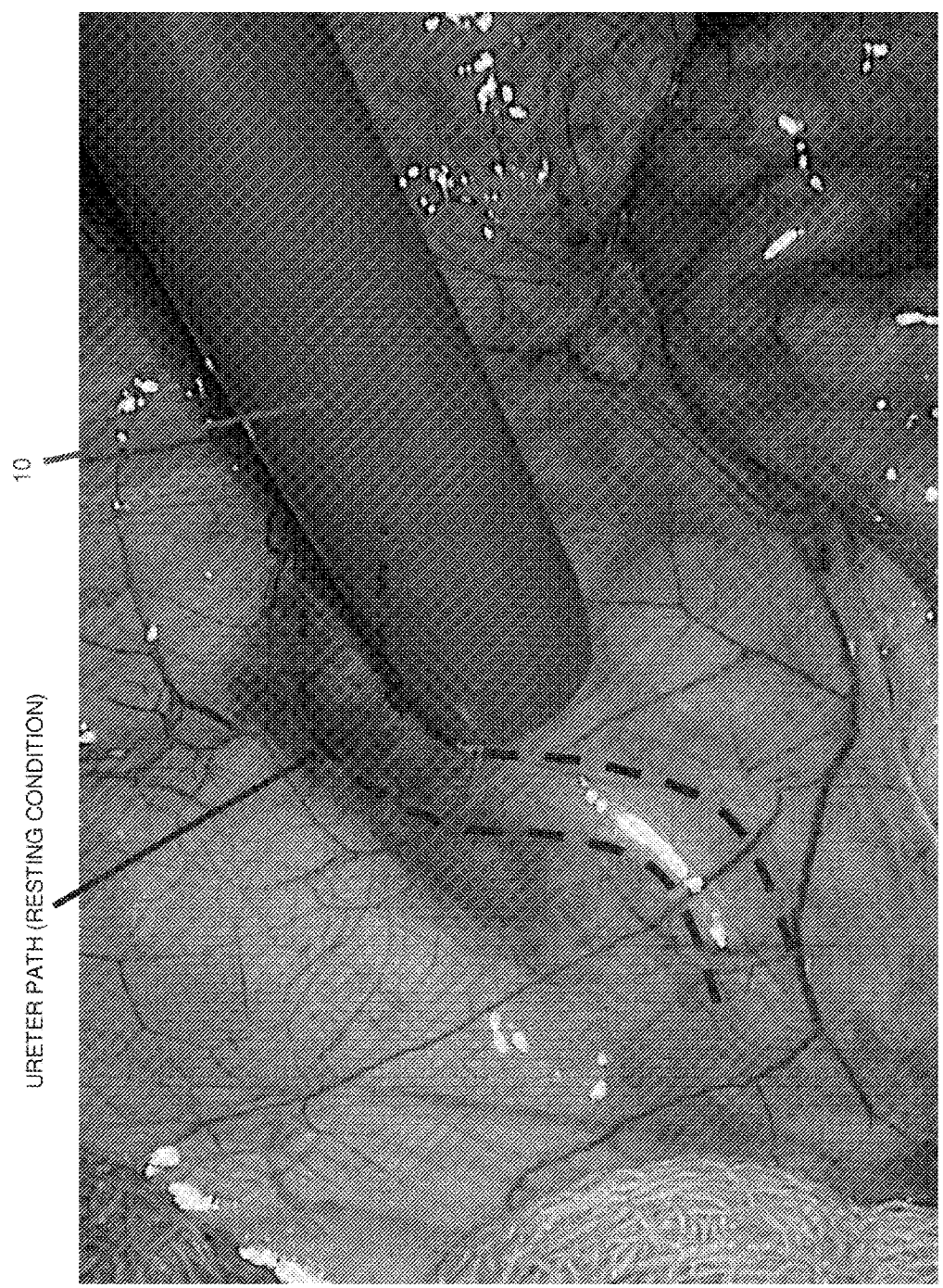
Figure 6:
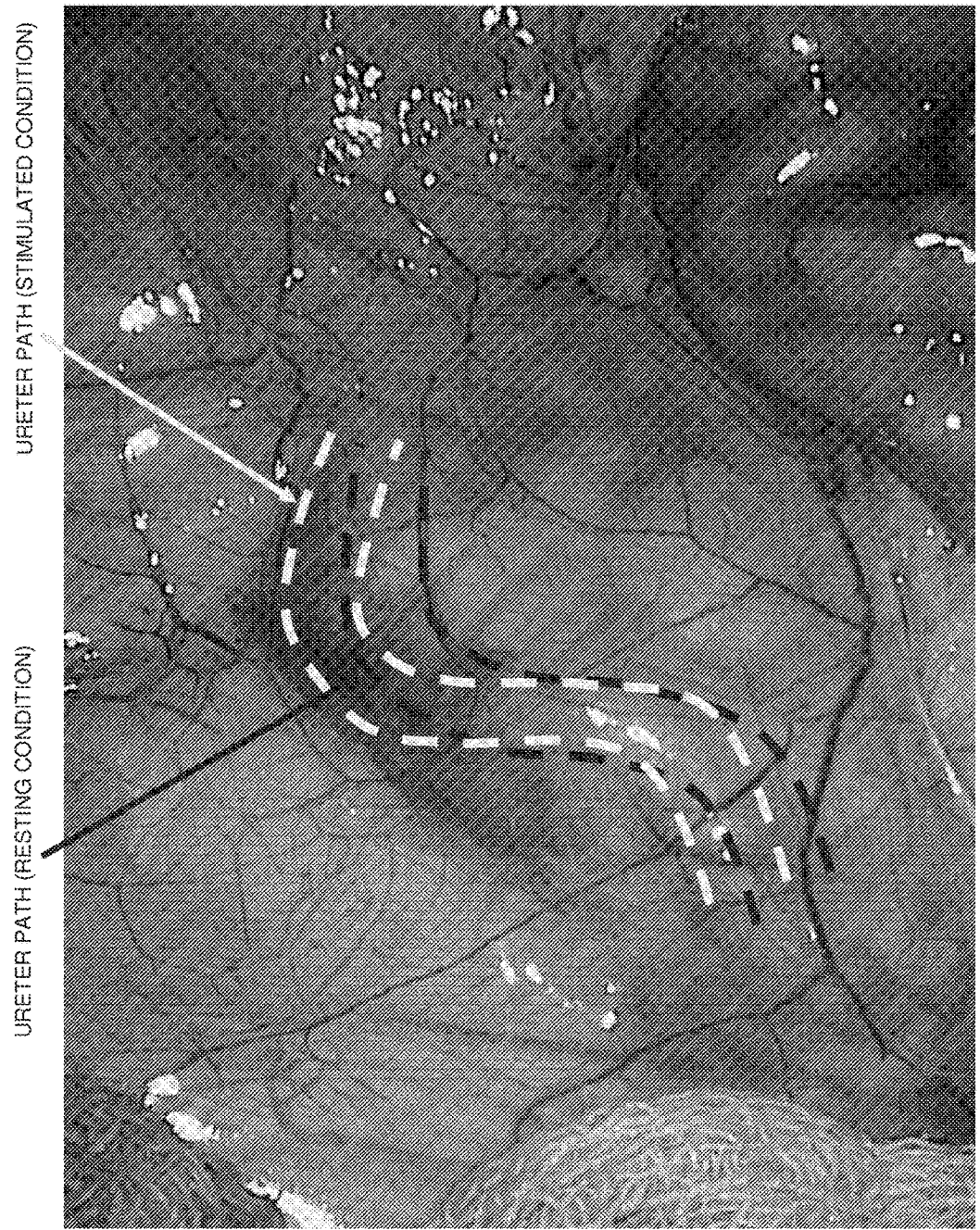
Figure 7:
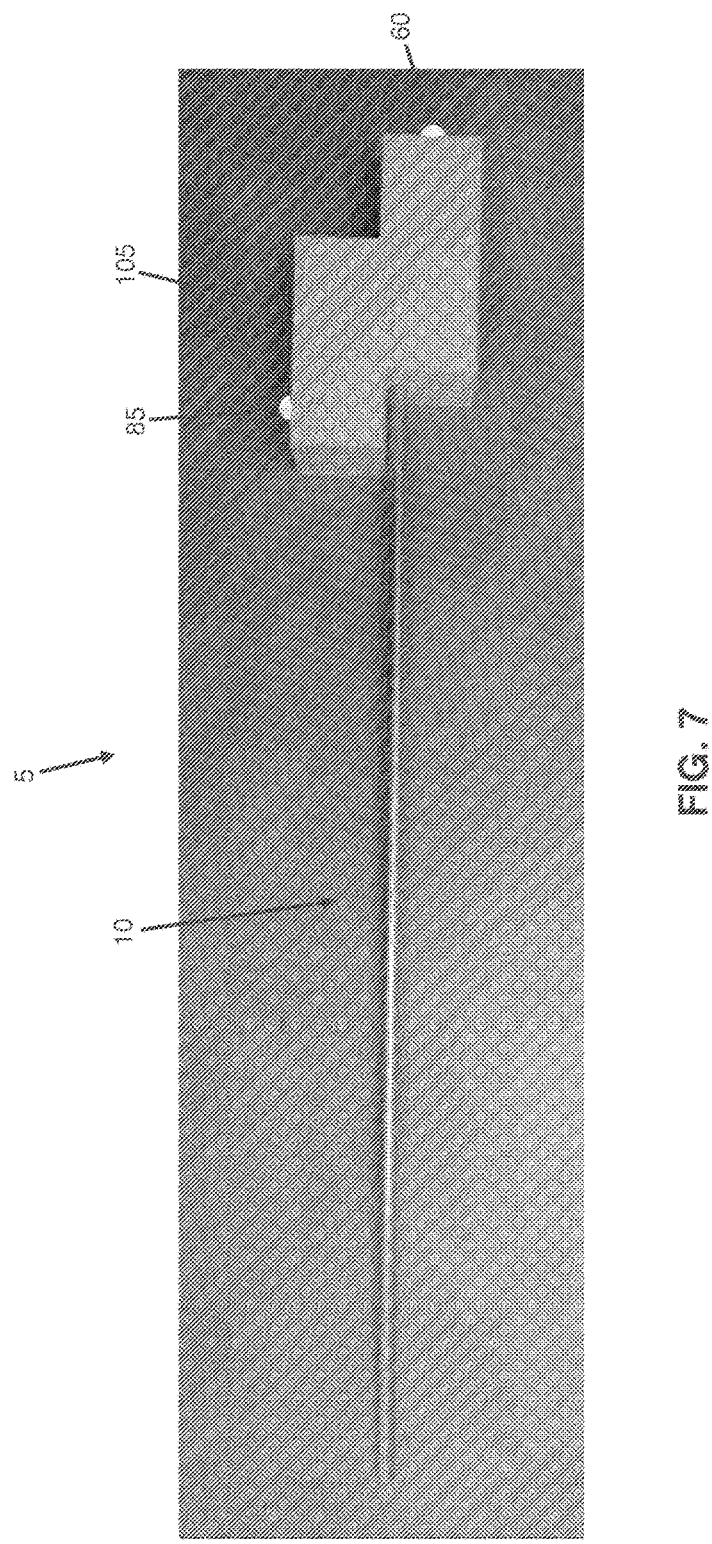
FIG. 7 is a schematic view showing another novel electrical stimulator formed in accordance with the present invention.
Figure 8:
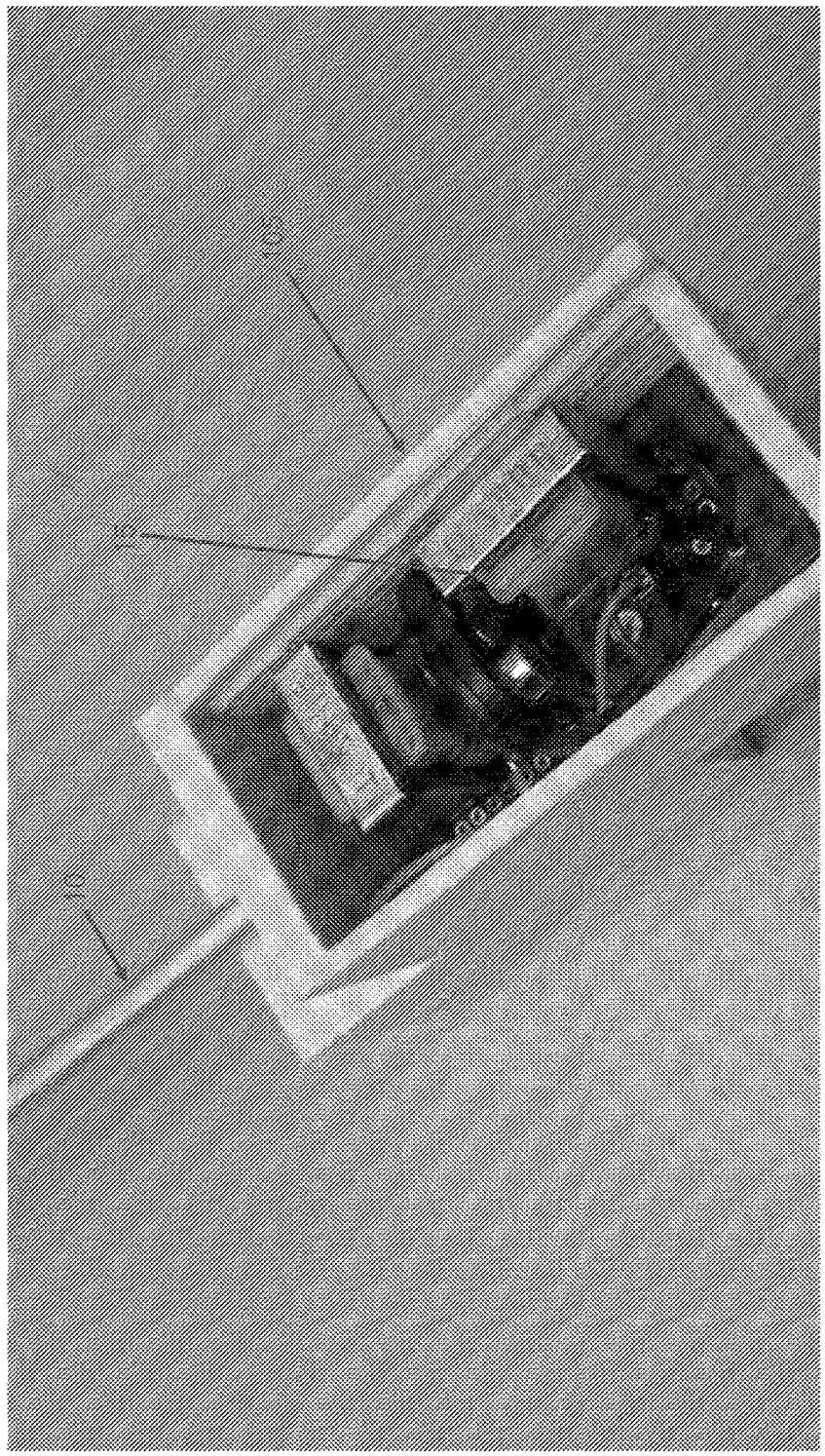
FIGS. 8-10 are schematic views showing construction details of the novel electrical stimulator shown in FIG. 7.
Figure 9:
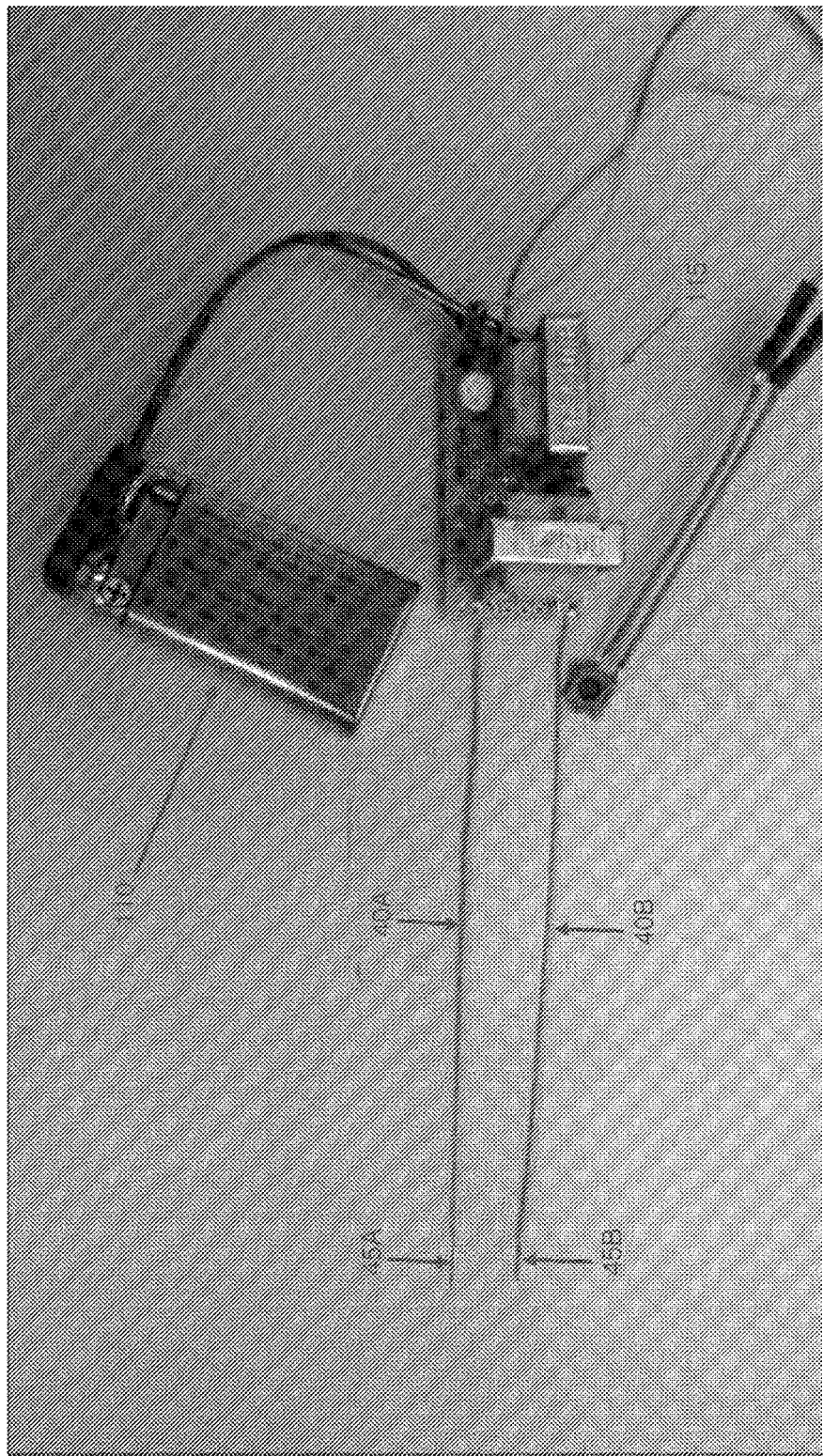
Figure 10:
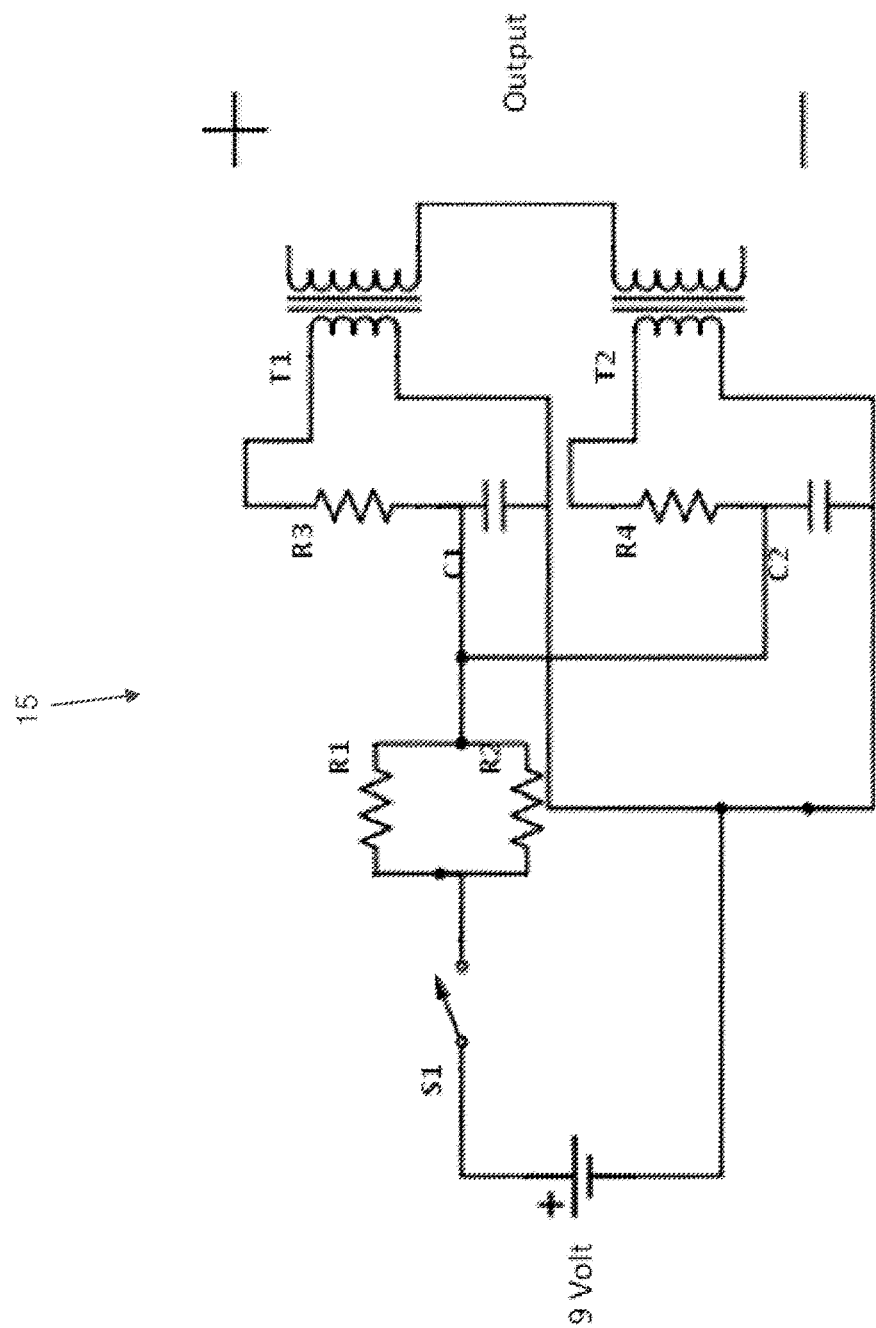

See FIGS. 4-6, which show (i) the natural path of a ureter in an unstimulated condition (FIG. 4); (ii) the probe 10 positioned against the ureter but before the electrical signal is applied to the tissue (FIG. 5); and (iii) the path of the ureter a few moments after electrical stimulation has been applied to the tissue (FIG. 6).

If at any time during the procedure, re-confirmation of ureter positioning needs to performed, the surgeon simply re-inserts probe 10 to the surgical site and repeats the foregoing procedure.

Once the surgical procedure is complete, probe 10 may be disconnected from power supply 15 and disposed of.

In another preferred form of the present invention, the electrical signal provided by power supply 15 has a preset pulse width (e.g., 100 milliseconds), a preset pulse frequency (e.g., 1 Hz) and a preset pulse intensity (e.g., 200 V). Using a "preset" electrical signal can have certain advantages, e.g., depending on target tissue(s), safety concerns, etc.

And in another preferred form of the present invention, the electrical signal provided by power supply 15 can be produced at a preset interval and for a preset duration (i.e., a preset pulse rate and a preset pulse width) of milliseconds, microseconds or seconds when active, so as to generate a rhythmic twitch in the target tissue.

Alternatively, power supply 15 can be configured to provide a single continuous signal when active so as to generate a sustained contraction in the target tissue.

Integrated Construction

In another preferred form of the present invention, and looking now at FIGS. 7-10, novel electrical stimulator 5 may incorporate power supply 15 into probe 10 so that the entire device is lightweight and handheld and fully disposable. In this case cable 20 may be omitted. More particularly, in this form of the invention, probe 10 may include an enlarged handle 105 carrying power supply 15 therein. By way of example but not limitation, power supply 15 may comprise a 9 V battery 110 and appropriate control electronics 115 for providing the desired electrical signal at electrode tips 45A, 45B.

In this form of the invention, the electrical signal provided by power supply 15 preferably has a preset pulse width (e.g., 100 milliseconds), a preset pulse frequency (e.g., 1 Hz) and a preset pulse intensity (e.g., 200 V), so that the only actions required of the user are (i) turning the device on or off via on/off switch 60, (ii) contacting the target tissue with electrode tips 45A, 45B, and (iii) pressing activate button 85 when the electrical signal is to be delivered to the tissue.

However, if desired, electrical stimulator 5 may also be constructed so that the electrical signal provided by power supply 15 has a variable pulse width, variable pulse frequency, variable pulse intensity and variable pulse amperage, in which case electrical stimulator 5 includes an appropriate pulse width control 70, an appropriate pulse frequency control 75 and an appropriate pulse intensity control 80.

In this form of the invention, the entire electrical stimulator 5 (including probe 10 and power supply 15) may be disposed of at the conclusion of the procedure.

Additional Constructions

In the foregoing disclosure, electrical stimulator 5 is described as comprising two electrodes, i.e., electrode tips 45A, 45B. In general, such a "bipolar" construction is preferred since it provides a more specific localization and a more localized current when attempting to target a smaller field and tissue. However, it is also anticipated that electrical stimulator 5 may comprise a "monopolar" construction having only one electrode tip, with the "return" being provided by a grounding pad.

In another form of the present invention, electrical stimulator 5 may comprise a relatively short probe 10 which is connected to an independent power supply 15 via cable 20. In this construction, probe 10 may be inserted into the abdominal cavity through a 5 mm trocar port using graspers (including robotic graspers) and may be thereafter manipulated by those graspers so as to apply electrical stimulation to the tissue which is believed to be the ureter so as to confirm ureter presence as well as the ureter path.

And in another form of the present invention, electrical stimulator 5 may be used in conjunction with an electromyogram (EMG) probe which detects electrical signals from a ureter's peristalsis and converts them into an audio signal. More particularly, in this form of the invention, and looking now at FIG. 11, there is provided an electromyogram (EMG) probe 120 which comprises an electromyogram (EMG) sensor 125 on the distal tip of electromyogram (EMG) probe 120. Signals detected by electromyogram (EMG) sensor 125 are relayed (via a cable 130) to a base unit 135 which converts those signals into an audio signal. Thus, in this form of the invention, electrical stimulator 5 is used to apply an electrical signal to the tissue which is believed to be the ureter, and the surgeon can then (i) visually observe the muscular response of the ureter, whereby to confirm ureter presence as well as the ureter path, and/or (ii) listen to the output of base unit 130, whereby to confirm ureter presence.

Additional Applications

The novel electrical stimulator of the present invention may also be used for purposes other than identifying the ureter.

By way of example but not limitation, the electrical stimulator may be incorporated on the end of a catheter or endoscope for use in other fields of "smooth muscle" stimulation or non-cauterizing electrical energy delivery. In one exemplary use, the electrical stimulator may be passed through the working channel of an endoscope and used to stimulate target tissues to confirm visual findings of the smooth muscle sphincter of the bile and pancreatic ducts.

Inasmuch as the electrical stimulator is able to stimulate both "skeletal muscle" and "smooth muscle", the electrical stimulator may also be used to determine muscle viability and reactivity in both minimally-invasive and open surgical settings. At the same time, the electrical stimulator can be used in these situations to assist in tissue/muscle identification and delineation, especially in unclear settings.

Modifications

While the present invention has been described in terms of certain exemplary preferred embodiments, it will be readily understood and appreciated by those skilled in the art that it is not so limited, and that many additions, deletions and modifications may be made to the preferred embodiments discussed herein without departing from the scope of the invention.

What is claimed is:

1. A method for identifying a ureter during a medical procedure, said method comprising:
    providing an electrical stimulator comprising:
        a shaft having at least one electrode; and
        a power supply connected to said at least one electrode for providing an electrical signal to said at least one electrode;
    advancing said shaft so that said at least one electrode contacts tissue in the vicinity of the ureter;
    operating said power supply so that said electrical signal is applied to the tissue to stimulate contraction of smooth tissue of the ureter; and
    visually observing contraction of the tissue to determine the presence of a ureter in the tissue.

2. A method according to claim 1 wherein said electrical signal is a low-level pulsatile electrical current.

3. A method according to claim 1 wherein said electrical signal has a pulse width of 25-300 milliseconds.

4. A method according to claim 1 wherein said electrical signal has a pulse frequency of 1-5 Hz.

5. A method according to claim 1 wherein said electrical signal has a pulse intensity of 60 mV-500 V.

6. A method according to claim 1 wherein said electrical signal has a pulse amperage of 5-200 mA.

7. A method according to claim 1 wherein the parameters of said electrical signal are adjustable by a user.

8. A method according to claim 1 wherein the parameters of said electrical signal are preset.

9. A method according to claim 1 wherein said electrical signal is a low-level continuous electrical current.

10. A method according to claim 1 wherein said power supply is connected to said shaft by an external cable.

11. A method according to claim 1 wherein said shaft comprises a housing, and further wherein said power supply is disposed within said housing.

12. A method according to claim 1 wherein said electrical stimulator comprises a bipolar construction, and further wherein said at least one electrode comprises two electrodes.

13. A method according to claim 1 wherein said electrical stimulator comprises a monopolar construction, and further wherein said at least one electrode comprises one electrode.

14. A method according to claim 1 wherein said shaft is advanced through a cannula.

15. A method according to claim 1 wherein said shaft is advanced through an endoscope.

16. A method according to claim 1 wherein said shaft is advanced using graspers.

17. A method according to claim 1 further comprising visually observing the tissue to determine the path of a ureter in the tissue.

18. A method according to claim 1 further comprising monitoring the tissue with an electromyogram (EMG) probe so as to detect electrical signals from a ureter's peristalsis.

19. A method according to claim 18 wherein detected electrical signals from a ureter's peristalsis are converted into an audio signal presented to a user.

* * * * *